(12) United States Patent
Vilsmeier

(10) Patent No.: US 9,724,539 B2
(45) Date of Patent: Aug. 8, 2017

(54) DOSE DISTRIBUTION DISPLAY METHOD USING COLOURS

(75) Inventor: Stefan Vilsmeier, Munich (DE)

(73) Assignee: Brainlab AG, Munich (DE)

( * ) Notice: Subject to any disclaimer, the term of this patent is extended or adjusted under 35 U.S.C. 154(b) by 277 days.

(21) Appl. No.: 14/347,145

(22) PCT Filed: Sep. 30, 2011

(86) PCT No.: PCT/EP2011/067184
§ 371 (c)(1),
(2), (4) Date: Mar. 25, 2014

(87) PCT Pub. No.: WO2013/044992
PCT Pub. Date: Apr. 4, 2013

(65) Prior Publication Data
US 2014/0232740 A1 Aug. 21, 2014

(51) Int. Cl.
*A61N 5/10* (2006.01)
*G06T 11/00* (2006.01)
*G06T 19/20* (2011.01)

(52) U.S. Cl.
CPC .......... *A61N 5/1031* (2013.01); *G06T 11/001* (2013.01); *G06T 19/20* (2013.01);
(Continued)

(58) Field of Classification Search
CPC .......... G06T 11/001; G06T 2219/2012; G06T 2207/10081; H04N 1/6058; H04N 1/6075;
(Continued)

(56) References Cited

U.S. PATENT DOCUMENTS 5,892,691 A * 4/1999 Fowler .................... G06T 19/20
345/619
2006/0153441 A1* 7/2006 Li ....................... H04N 1/40068
382/162
(Continued)

FOREIGN PATENT DOCUMENTS

WO 03/038725 5/2003
WO 2011/059554 5/2011

OTHER PUBLICATIONS

Soh J, Turinsky AL, Trinh QM, Chang J, Sabhaney A, Dong X, Gordon PM, Janzen RP, Hau D, Xia J, Wishart DS. Spatiotemporal integration of molecular and anatomical data in virtual reality using semantic mapping. Int. J. Nanomedicine. Jan. 1, 2009;4:79-89.*
(Continued)

*Primary Examiner* — Sultana M Zalalee
(74) *Attorney, Agent, or Firm* — Tucker Ellis LLP

(57) ABSTRACT

The invention is directed to a data processing method of displaying a radiation dose distribution in tissue of a patient and a corresponding program and computer running the program, the steps of the method being executed by a computer and comprising:
a) acquiring medical image data comprising medical image information describing an anatomical body part;
b) acquiring, based on the medical image data, irradiation eligibility data comprising irradiation eligibility information describing an eligibility class to which the anatomical body part belongs, the eligibility class describing the eligibility of the anatomical body part for irradiation with treatment radiation;
c) acquiring dose distribution data comprising dose distribution information describing a radiation dose distribution in the anatomical body part;
d) displaying, on a display device, the dose distribution information in the medical image information based on
(Continued)

the irradiation eligibility data and based on using a color range which represents the dose distribution information.

20 Claims, 1 Drawing Sheet

(52) U.S. Cl.
CPC ............... *G06T 2207/30004* (2013.01); *G06T 2219/2012* (2013.01)

(58) Field of Classification Search
CPC ........ H04N 9/3182; H04N 9/643; H04N 9/76; A61N 5/1031; A61N 5/103; A61N 2005/1072; A61N 5/1037; A61N 5/1071; G06F 17/3025; G06F 17/3053
See application file for complete search history.

(56) References Cited

U.S. PATENT DOCUMENTS

| | | | |
|---|---|---|---|
| 2010/0042438 A1* | 2/2010 | Moore | G06F 19/18 705/3 |
| 2011/0063288 A1* | 3/2011 | Valadez | G06T 15/08 345/419 |
| 2011/0107270 A1* | 5/2011 | Wang | G06F 19/3437 715/850 |
| 2013/0230225 A1* | 9/2013 | Waechter-Stehle | A61B 6/463 382/131 |

OTHER PUBLICATIONS

International Search Report and Written Opinion for International Application No. PCT/EP2011/067184 dated Aug. 30, 2012.
International Preliminary Report on Patentability, PCT/EP2011/067184, Date of issuance: Apr. 1, 2014 pp. 1-6.

* cited by examiner

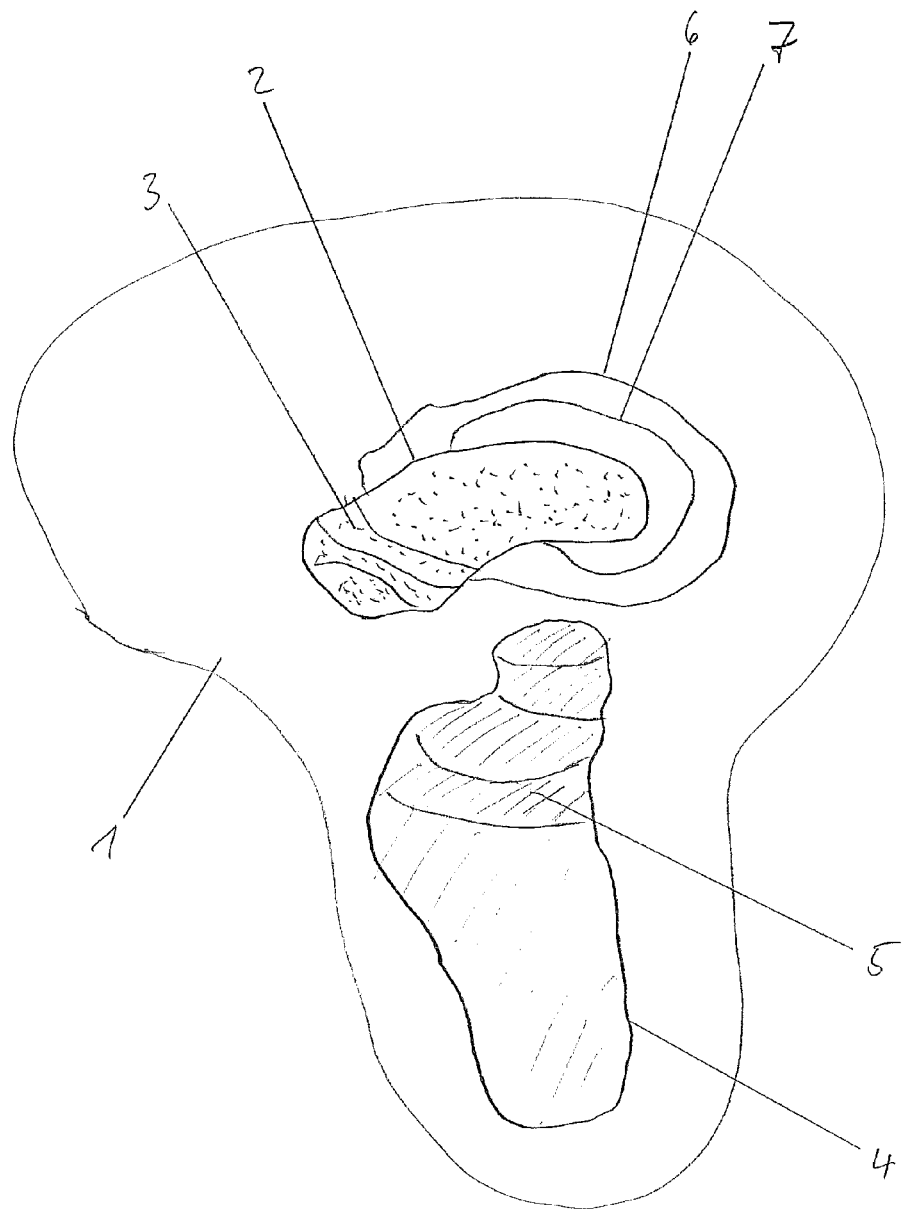

DOSE DISTRIBUTION DISPLAY METHOD USING COLOURS

RELATED APPLICATION DATA

This application is a national phase application of International Application No. PCT/EP2011/067184 filed Sep. 30, 2011 and published in the English language.

The present invention is directed to a method, in particular data processing method of displaying a radiation dose distribution according to the independent claim.

When planning a radiotherapy treatment for a specific patient, the distribution of the radiation dose in tissue of the patient's body is generally determined before the treatment starts. In particular, a radiation dose caused in different anatomical regions or types of tissue has to be determined beforehand. In general, a graphical display or a dose distribution is displayed within medical image information about the anatomical regions of interest. The regions of interest comprise a target region and off-target regions such as healthy tissue and critical structures. The information about the dose distribution is normally displayed by using a colour scheme (colour range). In current techniques, the same colour scheme is used for both target volumes, healthy tissue and critical structures. This leads to problems in visually differentiating between the type of region of interest to which a graphic representation of dose distribution information is assigned.

A problem to be solved by the present invention thus is to simplify visual recognition of the type of region of interest to which graphical dose distribution information is assigned.

This problem is solved by the subject-matter of any appended independent claim. Advantages, advantageous features, advantageous embodiments and advantageous aspects of the present invention are disclosed in the following and contained in the subject-matter of the dependent claims. Different advantageous features can be combined in accordance with the invention as long as technically sensible and feasible. In particular, a feature of one embodiment which has the same or similar function of another feature of another embodiment can be exchanged. In particular, a feature of one embodiment which supplements a further function to another embodiment can be added to the other embodiment.

Within the framework of the invention, computer program elements can be embodied by hardware and/or software (this includes firmware, resident software, micro-code, etc.). Within the framework of the invention, computer program elements can take the form of a computer program product which can be embodied by a computer-usable, in particular computer-readable data storage medium comprising computer-usable, in particular computer-readable program instructions, "code" or a "computer program" embodied in said data storage medium for use on or in connection with the instruction-executing system. Such a system can be a computer; a computer can be a data processing device comprising means for executing the computer program elements and/or the program in accordance with the invention, in particular a data processing device comprising a digital processor (central processing unit—CPU) which executes the computer program elements and optionally a volatile memory (in particular, a random access memory—RAM) for storing data used for and/or produced by executing the computer program elements. Within the framework of the present invention, a computer-usable, in particular computer-readable data storage medium can be any data storage medium which can include, store, communicate, propagate or transport the program for use on or in connection with the instruction-executing system, apparatus or device. The computer-usable, in particular computer-readable data storage medium can for example be, but is not limited to, an electronic, magnetic, optical, electromagnetic, infrared or semiconductor system, apparatus or device or a medium of propagation such as for example the Internet. The computer-usable or computer-readable data storage medium could even for example be paper or another suitable medium onto which the program is printed, since the program could be electronically captured, for example by optically scanning the paper or other suitable medium, and then compiled, interpreted or otherwise processed in a suitable manner. Preferably, the data storage medium is a non-volatile data storage medium. The computer program product and any software and/or hardware described here form the various means for performing the functions of the invention in the example embodiments. The computer and/or data processing device can in particular include a guidance information device which includes means for outputting guidance information. The guidance information can be outputted, for example to a user, visually by a visual indicating means (for example, a monitor and/or a lamp) and/or acoustically by an acoustic indicating means (for example, a loudspeaker and/or a digital speech output device) and/or tactilely by a tactile indicating means (for example, a vibrating element or vibration element incorporated into an instrument).

The present invention relates to the field of controlling a treatment beam The present invention relates to the field of medicine and in particular to the use of beams, in particular radiation beams, to treat parts of a patient's body, which are also called treatment beams. A treatment beam treats body parts which are to be treated, which are referred to in the following as "treatment body parts". These body parts are in particular parts of a patient's body, i.e. anatomical body parts. Ionising radiation is in particular used for the purpose of treatment. In particular, the treatment beam comprises or consists of ionising radiation. The ionising radiation comprises or consists of particles (for example, sub-atomic particles or ions) or electro-magnetic waves which are energetic enough to detach electrons from atoms or molecules and so ionise them. Examples of such ionising radiation are X-rays, high-energy particles (high-energy particle beams) and/or ionizing radiation emitted from a radioactive element. The treatment radiation, in particular the treatment beam, is in particular used in radiation therapy or radiotherapy, in particular in the field of oncology. For treating cancer in particular, parts of the body comprising a pathologic structure or tissue such as a tumour are treated using ionising radiation. The tumour is then an example of a treatment body part.

The treatment beam is preferably controlled such that it passes through the treatment body part. However, the treatment beam can have a negative effect on body parts outside the treatment body part. These body parts are referred to here as "outside body parts". Generally, a treatment beam has to pass through outside body parts in order to reach and so pass through the treatment body part.

With respect to background A, reference is made to the following two web pages:
http://www.elekta.com/healthcare_us_elekta_vmat.php and
http://www.varian.com/us/oncology/treatments/treatment-techniques/rapidarc.

In order to determine the position or visualize of the treatment body parts, analytical devices such as x-ray devices, CT devices or MRT devices are used to generate analytical images (such as x-ray images or MRT images) of the body. Analytical devices are in particular devices for analysing a patient's body, for instance by using waves and/or radiation and/or energy beams, in particular electromagnetic waves and/or radiation, ultrasound waves and/or particles beams. Analytical devices are in particular devices which generate images (for example, two-dimensional or three-dimensional images) of the patient's body (in particular, internal structures and/or anatomical parts of the patient's body) by analysing the body. Analytical devices are in particular used in medical diagnosis, in particular in radiology. However, it can be difficult to identify the treatment body part within the analytical image. It can in particular be easier to identify an indicator body part which correlates with changes in the position of the treatment body part and in particular the movement of the treatment body part. Thus, tracking an indicator body part allows a movement of the treatment body part to be tracked on the basis of a known correlation between the changes in the position (in particular the movements) of the indicator body part and the treatment body part.

In the field of medicine, imaging methods are used to generate image data (for example, two-dimensional or three-dimensional image data) of anatomical structures (such as soft tissues, bones, organs, etc.) of the human body. Medical imaging methods are understood to mean advantageously apparatus-based imaging methods (so-called medical imaging modalities and/or radiological imaging methods), such as for instance computed tomography (CT) and cone beam computed tomography (CBCT; in particular volumetric CBCT), x-ray tomography, magnetic resonance tomography (MRT or MRI), conventional x-ray, sonography and/or ultrasound examinations, and positron emission tomography. Analytical devices are in particular used to generate the image data in apparatus-based imaging methods. The imaging methods are in particular used for medical diagnostics, to analyse the anatomical body in order to generate images which are described by the image data. The imaging methods are in particular used to detect pathological changes in the human body. However, some of the changes in the anatomical structure, in particular the pathological changes in the structures (tissue), may not be detectable and in particular may not be visible in the images generated by the imaging methods. A tumour for example represents an example of a change in an anatomical structure. If the tumour grows, it may then be said to represent an expanded anatomical structure. This expanded anatomical structure may not be detectable; in particular, only a part of the expanded anatomical structure may be detectable. Primary/high-grade brain tumours are for example usually visible on MRI scans when contrast agents are used to infiltrate the tumour. The MRI scans represent an example of an imaging method. In the case of MRI scans of such brain tumours, the signal enhancement in the MRI images (due to the contrast agents infiltrating the tumour) is considered to represent the solid tumour mass. Thus, the tumour is detectable and in particular discernable in the image generated by the imaging method. In addition to these tumours, referred to as "enhancing" tumours, it is thought that approximately 10% of brain tumours are not discernable on a scan and are in particular not visible to a user looking at the images generated by the imaging method.

The method in accordance with the invention is in particular a data processing method. The data processing method is preferably performed using technical means, in particular a computer. In particular, the data processing method is executed by or on the computer. The computer in particular comprises a processor and a memory in order to process the data, in particular electronically and/or optically. The calculating steps described are in particular performed by a computer. Determining or calculating steps are in particular steps of determining data within the framework of the technical data processing method, in particular within the framework of a program. A computer is in particular any kind of data processing device, in particular electronic data processing device. A computer can be a device which is generally thought of as such, for example desktop PCs, notebooks, netbooks, etc., but can also be any programmable apparatus, such as for example a mobile phone or an embedded processor. A computer can in particular comprise a system (network) of "sub-computers", wherein each sub-computer represents a computer in its own right. The term of computer encompasses a cloud computer, in particular a cloud server. The term of cloud computer encompasses cloud computer system in particular comprises a system of at least one cloud computer, in particular plural operatively interconnected cloud computers such as a server farm. Preferably, the cloud computer is connected to a wide area network such as the world wide web (WWW). Such a cloud computer is located in a so-called cloud of computers which are all connected to the world wide web. Such an infrastructure is used for cloud computing which describes computation, software, data access and storage services that do not require end-user knowledge of physical location and configuration of the computer that delivers a specific service. In particular, the term "cloud" is used as a metaphor for the internet (world wide web). In particular, the cloud provides computing infrastructure as a service (IaaS). The cloud computer may function as a virtual host for an operating system and/or data processing application which is used for executing the inventive method. Preferably, the cloud computer is an elastic compute cloud (EC2) provided by Amazon Web Services™. A computer in particular comprises interfaces in order to receive or output data and/or perform an analogue-to-digital conversion. The data are in particular data which represent physical properties and/or are generated from technical signals. The technical signals are in particular generated by means of (technical) detection devices (such as for example devices for detecting marker devices) and/or (technical) analytical devices (such as for example devices for performing imaging methods), wherein the technical signals are in particular electrical or optical signals. The technical signals represent in particular the data received or outputted by the computer.

The expression "acquiring data" encompasses in particular (within the framework of a data processing method) the scenario in which the data are determined by the data processing method or program. Determining data in particular encompasses measuring physical quantities and transforming the measured values into in particular digital data and/or computing the data by means of a computer, in particular computing the data within the method of the invention. The meaning of "acquiring data" in particular also encompasses the scenario in which the data are received or retrieved by the data processing method or program, for example from another program, a previous method step or a data storage medium, in particular for further processing by the data processing method or program. Thus, "acquiring data" can also for example mean waiting to receive data and/or receiving the data. The received data can for example be inputted via an interface. "Acquiring data" can also mean that the data processing method or program performs steps in order to (actively) receive or retrieve the data from a data source, for instance a data storage medium (such as for example a ROM, RAM, database, hard disc, etc.) or via the interface (for instance, from another computer or a network). The data can achieve the state of being "ready for use" by performing an additional step before the acquiring step. In accordance with this additional step, the data are generated in order to be acquired. The data are in particular detected or captured (for example, by an analytical device). Alternatively or additionally, the data are inputted in accordance with the additional step, for instance via interfaces. The data generated can in particular be inputted (for instance, into the computer). In accordance with the additional step (which precedes the acquiring step), the data can also be provided by performing the additional step of storing the data in a data storage medium (such as for example a ROM, RAM, CD and/or hard drive), such that they are ready for use within the framework of the method or program in accordance with the invention. Thus, "acquiring data" can also involve commanding a device to obtain and/or provide the data to be acquired. The acquiring step in particular does not involve an invasive step which would represent a substantial physical interference with the body requiring professional medical expertise to be carried out and entailing a substantial health risk even when carried out with the required professional care and expertise. Acquiring, in particular determining, data in particular does not involve a surgical step and in particular does not involve a step of treating a human or animal body using surgery or therapy. This also applies in particular to any steps directed to determining data. In order to distinguish the different data used by the present method, the data are denoted (i.e. referred to) as "XY data" and the like and are defined by the information which they describe.

Preferably, the inventive method is at least partly executed by a computer. That is, all steps or just some of the steps (i.e. less than a total number of steps) of the inventive method may be executed by a computer.

The inventive method is a data processing method of displaying irradiation dose distribution. The radiation dose distribution represents information about the distribution of a radiation dose accumulated in tissue of a patient due to radiotherapy. In the framework of this disclosure, the term of dose encompasses both the term of energy dose and equivalent dose. Preferably, medical image data is acquired which comprises medical image information describing an anatomical body part of the patient. Medical image data is image data which is produced by applying a medical imaging method to the patient's body.

Preferably, irradiation eligibility data is acquired based on the medical image data. The irradiation eligibility data comprises irradiation eligibility information which in particular describes an eligibility class to which the anatomical body part or constituents of the anatomical body part belong. The eligibility class describes the eligibility of the anatomical body part or its constituents for irradiation with treatment radiation. The term of eligibility describes in particular whether and in particular how much it is desirable to irradiate the anatomical body part or its constituents with treatment radiation. In other words, the eligibility class is a measure for desirability of irradiation. In radiotherapy, one has to discern between a target region which represents the above-described treatment body part and off-target regions which encompass in general all body parts which are not part of a target region. The off-target regions may be, for example, healthy tissue or critical structures. In radiotherapy it is generally desirable to keep a dose applied to healthy tissue as small as possible while it is normally inevitable to irradiate the healthy tissue since the treatment beams normally have to pass through healthy tissue in order to reach the target region. Critical structures are in the framework of this disclosure also called critical regions, healthy tissue is also called a healthy region. A critical region is in particular a region which must not be irradiated with treatment radiation in order to avoid undesired damage to the patient's body. Critical regions comprise for example the heart or functional areas of the brain, a damage to which may be fatal or unrepairable and associated with undesired effects on the patient's quality of life. The tissue of the patient's body may therefore be grouped into in particular three eligibility classes. Preferably, an eligibility class is assigned each to healthy regions, critical regions and target regions. Alternatively or additionally, a specific eligibility class may be assigned to off-target regions. Preferably, a unique numeric value is assigned to each illegibility class. Further preferably, the illegibility classes assigned to target regions, off-target regions, healthy regions and critical regions are unique per such region or per such kind of region. A generic term which encompasses all these kinds of regions is in the framework of this invention called eligibility region.

The irradiation eligibility data is acquired preferably based on information about the position of the eligibility regions in the medical image and in particular information about the radio-therapy treatment to be carried out such as the beam energy, type of beam, type of beam source and type of disease to be treated.

Preferably, dose distribution data is acquired which comprises dose distribution information describing a radiation dose distribution in the anatomical body part. Preferably, the dose distribution data is acquired based on the medical image data. In particular, absorption data comprising absorption information describing an absorption of the treatment radiation by the anatomical body part may be acquired based on the medical image data. The absorption information acquired based on the medical image data is preferably represented by Hounsfield units which are a measure of absorption of the ionizing radiation used for the imaging method with which the medical image data are generated in relation to the image contrast, in particular in relation to its grey shades. By providing information about the type of treatment radiation and in particular the beam energy, the corresponding absorption of the treatment radiation by the anatomical body part may be determined The dose distribution data then is preferably acquired based on the absorption data.

Eligibility regions to which different eligibility classes have been assigned may overlap or not overlap. It is to be noted that data processing in the framework of the invention can be carried out in in particular two or in particular three spatial dimensions. Preferably, however, the data processing is carried out in three spatial dimensions. An overlap may therefore be defined as a two-dimensional or three-dimensional intersection of the eligibility regions.

Preferably, the dose distribution information is displayed on a display device. Further preferably, the dose distribution information is displayed in the medical image information in particular by highlighting. The display device in particular is any kind of standard monitors such as a cathode ray tube monitor or an LCD display. Displaying the dose distribution information is preferably based on using a colour range for the highlighting which represents the dose distribution information. In particular, specific dose values are uniquely assigned specific colours (also called colour values). Since the dose distribution information is to be displayed in a specific manner for each eligibility class (i.e. each type of eligibility region), displaying the dose distribution information is also based on the irradiation eligibility data. Preferably, a colour range is uniquely assigned to each eligibility class. In other words, a unique colour range is used for displaying the dose distribution information for each body part belonging to a specific eligibility class. The dose distribution information is preferably displayed such that it is displayed at the location of the associated body part or eligibility region in the image. In other words, the dose distribution is graphically overlaid over the body part for which it has been determined and with which it is associated. According to a specific embodiment of the invention, the colour range may be additionally assigned uniquely to specific anatomical regions. For example, the dose distribution information for different critical structures in the brain may be displayed in a colour range which is unique per specific critical structure.

A colour range is a range or interval of distinct colour values which each appear only once in the interval. Preferably, the colour range which is used for a specific eligibility class is disjoint to a colour range for any other eligibility class. The colour ranges and their property of being disjoint is preferably defined in a colour space such as a red-green-blue (RGB) colour space or a cyan-magenta-yellow-black (CMYK) colour space.

Preferably, the colour values in the colour range are normalized to represent a dose distribution value range which is unique to the colour range. For example, different dose distribution value ranges as described by the dose distribution information may be displayed with different, in particular disjoint, colour ranges.

Information about the colour range, in particular the colour values contained in the colour range, is preferably described by colour range information contained in colour range data. In other words, the colour range information describes a colour range usable for displaying dose distribution information, in particular dose values. More particularly, the colour range (the colour values) describe dose values. The colour range data is preferably acquired within the inventive method. The dose distribution data then preferably displayed based on (also) the colour range data.

Preferably, dose distribution range data is determined based on acquiring a maximum and a minimum dose distribution value contained in the dose distribution information. The dose distribution range data in particular comprises dose distribution range information which describes a range of dose distribution values to be displayed. Preferably, colour range partition data is acquired or determined based on the dose distribution range data. The colour range partition data in particular comprises partition information which describes a partitioning of the dose distribution range. Preferably, the dose distribution range is partitioned into disjoint classes or discrete values. Each disjoint class or discrete value is then assigned a colour value in the colour range. The dose distribution information is then preferably claimed based on the colour range partition data.

The invention also relates to a program which, when running on a computer or when loaded onto a computer, causes the computer to perform one or more or all of the method steps described herein and/or to a program storage medium on which the program is stored (in particular in a non-transitory form) and/or to a computer on which the program is running or into the memory of which the program is loaded and/or to a signal wave, in particular a digital signal wave, carrying information which represents the program, in particular the aforementioned program, which in particular comprises code means which are adapted to perform any or all of the method steps described herein. The computer on which the aforementioned program is running or into the memory of which the program is loaded preferably comprises a cloud computer.

In the following, an example embodiment of the present invention is described with reference to the FIGURE, which is merely to be regarded as an example of the invention without limiting the invention to this specific embodiment, wherein:

FIG. 1 shows a display or dose distribution information for anatomical regions of the human brain.

In FIG. 1, an outline of the application of the inventive method to a dose distribution in the human brain 1 is given. The dose distribution information in the target region 2 is displayed in a range of colours in the red range as indicated by dots 3. Specific classes of dose values are indicated by a respective red shading for each class.

The dose distribution information for the brain stem 4 is displayed in analogy to the dose distribution information for the target region but in shades of green, i.e. in the green colour range as indicated by stripes 5. The brain stem is an example of a critical region, the corresponding eligibility class in this case being assigned the green colour range.

Around the target region 2, contour lines 6, 7 representing isodose lines (i.e. lines of same dose value) are drawn in the blue colour range to indicate the dose distribution information in a healthy region.

As a further embodiment of the present invention, a further critical region occurring in the embodiment of FIG. 1 could be assigned the yellow colour range for displaying the dose distribution information for that further critical region. This would represent the case in which colour ranges are assigned uniquely per anatomical region and eligibility class.

An advantage of displaying the dose distribution information in the manner shown by FIG. 1 is that the person viewing the graphical representation is able to identify the eligibility regions of different eligibility class at first glance by virtue of the colour used for displaying the dose distribution information associated with the respective anatomical regions. Furthermore, the invention simplifies the process of visually comparing two alternative irradiation plans when placing them side-by-side.

The invention claimed is:

1. A data processing method of displaying a radiation dose distribution of a treatment radiation in tissue of a patient, the method being executed by a computer and comprising:
  acquiring medical image data comprising medical image information describing a plurality of anatomical body parts of the patient;
  acquiring, based on the medical image data, irradiation eligibility data comprising irradiation eligibility information describing an eligibility class to which each anatomical body part of the plurality of anatomical body parts belongs, each eligibility class describing a measure of desirability of irradiating a corresponding anatomical body part with the treatment radiation;
  acquiring dose distribution data comprising dose distribution information describing the radiation dose distribution in the plurality of anatomical body parts; and
  displaying, on a display device, the dose distribution information colorized in the medical image information and graphically overlaid with an image of the plurality of anatomical body parts, the displaying of the dose distribution information colorized in the medical image information being based on the irradiation eligibility data and based on using a color shading that represents the dose distribution information in the plurality of anatomical body parts, wherein, for each selected eligibility class, a unique color range is assigned to one or more anatomical body parts belonging to the each selected eligibility class for the displaying.

2. The method according to claim 1, comprising:
acquiring, based on the medical image data, absorption data comprising absorption information describing an absorption of the treatment radiation by the one or more anatomical body parts, wherein the absorption information is preferably represented by Hounsfield units.

3. The method according to claim 1, wherein the dose distribution data is acquired based on absorption data.

4. The method according to claim 3, wherein the color range is uniquely assigned to the eligibility class.

5. The method according to claim 1, comprising:
acquiring color range data comprising color range information describing a color range usable for displaying dose distribution information, in particular dose values.

6. The method according to claim 5, wherein the dose distribution data are displayed based on the color range data.

7. The method according to claim 6, wherein eligibility regions belonging to different eligibility classes overlap in two or three spatial dimensions or do not overlap in two or three spatial dimensions.

8. The method according to claim 6, wherein the color range for a specific eligibility class is disjoint to a color range for any other eligibility class.

9. The method according to claim 1, wherein the color range is defined in a red-green-blue color space or cyan-magenta-yellow-black color space.

10. The method according to claim 1, wherein each an eligibility class is assigned to a target region and an off-target region, the off-target region comprising in particular a healthy region and a critical region, wherein in particular each an eligibility class is assigned to a healthy region and a critical region.

11. The method according to claim 10, comprising:
determining, based on acquiring a maximum and minimum dose distribution value contained in the dose distribution information, dose distribution range data comprising dose distribution range information describing a range of dose distribution values to be displayed;
acquiring or determining, based on the dose distribution range data, color range partition data comprising partition information describing a partitioning of the dose distribution range;
displaying the dose distribution information based on the color range partition data.

12. The method according to claim 11, wherein the partitioning of the dose distribution range is a partitioning into disjoint classes or into discrete values.

13. The method according to claim 1, wherein the color range is normalized to represent a dose distribution value range which is unique to the color range.

14. The method according to claim 1, wherein the acquiring the irradiation eligibility data comprises:
acquiring the irradiation eligibility data comprising irradiation eligibility information describing:
a first eligibility class assigned to healthy tissue regions of the patient to which a first set of one or more anatomical body parts of the plurality of anatomical body parts belong, the first eligibility class describing a moderate measure of desirability of irradiating a corresponding anatomical body part member of the first eligibility class with the treatment radiation, wherein irradiation is acceptable but not desired;
a second eligibility class assigned to critical tissue regions of the patient to which a second set of one or more anatomical body parts of the plurality of anatomical body parts belong, the second eligibility class describing a low measure of desirability of irradiating a corresponding anatomical body part member of the second eligibility class with the treatment radiation, wherein irradiation is unacceptable and not desired; and
a third eligibility class assigned to target tissue regions of the patient to which a third set of one or more anatomical body parts of the plurality of anatomical body parts belong, the third eligibility class describing a high measure of desirability of irradiating a corresponding anatomical body part member of the third eligibility class with the treatment radiation, wherein irradiation is acceptable and desired.

15. The method according to claim 14, wherein the displaying comprises:
displaying, on the display device, the dose distribution information colorized in the medical image information and graphically overlaid with the image of the plurality of anatomical body parts based on:
a first color range assigned to the anatomical body parts belonging to the first eligibility class assigned to the healthy tissue regions of the patient and using a shading of the first color range, the shading of the first color range representing the dose distribution information in the anatomical body parts belonging to the first eligibility class assigned to the healthy tissue regions of the patient;
a second color range assigned to the anatomical body parts belonging to the second eligibility class assigned to the critical tissue regions of the patient and using a shading of the second color range, the shading of the second color range representing the dose distribution information in the anatomical body parts belonging to the second eligibility class assigned to the critical tissue regions of the patient, wherein the second color range is disjoint to the first color range; and
a third color range assigned to the anatomical body parts belonging to the third eligibility class assigned to the target tissue regions of the patient and using a shading of the third color range, the shading of the third color range representing the dose distribution information in the anatomical body parts belonging to the third eligibility class assigned to the target tissue regions of the patient, wherein the third color range is disjoint to the first and second color ranges.

16. The method according to claim 15, wherein:
the first color range assigned to the anatomical body parts belonging to the first eligibility class assigned to the healthy tissue regions of the patient comprises a blue color range, and the dose distribution information in the anatomical body parts belonging to the first eligibility class assigned to the healthy tissue regions of the patient is represented using a shading of the blue color range;
the second color range assigned to the anatomical body parts belonging to the second eligibility class assigned to the critical tissue regions of the patient comprises a green color range, and the dose distribution information in the anatomical body parts belonging to the second eligibility class assigned to the critical tissue regions of the patient is represented using a shading of the green color range; and the third color range assigned to the anatomical body parts belonging to the third eligibility class assigned to the target tissue regions of the patient comprises a red color range, and the dose distribution information in the anatomical body parts belonging to the third eligibility class assigned to the target tissue regions of the patient is represented using a shading of the red color range.

17. A computer program embodied on a non-transitory computer readable medium which, when running on a computer or when loaded onto a computer, causes the computer to perform a method of displaying a radiation dose distribution of a treatment radiation in tissue of a patient, comprising:
   acquiring medical image data comprising medical image information describing a plurality of anatomical body parts of the patient;
   acquiring, based on the medical image data, irradiation eligibility data comprising irradiation eligibility information describing an eligibility class to which each anatomical body part of the plurality of anatomical body parts belongs, each eligibility class describing a measure of desirability of irradiating a corresponding anatomical body part with the treatment radiation;
   acquiring dose distribution data comprising dose distribution information describing the radiation dose distribution in the plurality of anatomical body parts; and
   displaying, on a display device, the dose distribution information colorized in the medical image information and graphically overlaid with an image of the plurality of anatomical body parts, the displaying of the dose distribution information colorized in the medical image information being based on the irradiation eligibility data and based on using a color shading that represents the dose distribution information in the plurality of anatomical body parts,
   wherein, for each selected eligibility class, a unique color range is assigned to one or more anatomical body parts belonging to the each selected eligibility class for the displaying.

18. The computer program according to claim 17, wherein:
   the acquiring the irradiation eligibility data comprises:
      acquiring the irradiation eligibility data comprising irradiation eligibility information describing:
         a first eligibility class assigned to healthy tissue regions of the patient to which a first set of one or more anatomical body parts of the plurality of anatomical body parts belong, the first eligibility class describing a moderate measure of desirability of irradiating a corresponding anatomical body part member of the first eligibility class with the treatment radiation, wherein irradiation is acceptable but not desired;
         a second eligibility class assigned to critical tissue regions of the patient to which a second set of one or more anatomical body parts of the plurality of anatomical body parts belong, the second eligibility class describing a low measure of desirability of irradiating a corresponding anatomical body part member of the second eligibility class with the treatment radiation, wherein irradiation is unacceptable and not desired; and
         a third eligibility class assigned to target tissue regions of the patient to which a third set of one or more anatomical body parts of the plurality of anatomical body parts belong, the third eligibility class describing a high measure of desirability of irradiating a corresponding anatomical body part member of the third eligibility class with the treatment radiation, wherein irradiation is acceptable and desired; and
   the displaying comprises:
      displaying, on the display device, the dose distribution information colorized in the medical image information and graphically overlaid with the image of the plurality of anatomical body parts based on:
         a first color range assigned to the anatomical body parts belonging to the first eligibility class assigned to the healthy tissue regions of the patient and using a shading of the first color range, the shading of the first color range representing the dose distribution information in the anatomical body parts belonging to the first eligibility class assigned to the healthy tissue regions of the patient;
         a second color range assigned to the anatomical body parts belonging to the second eligibility class assigned to the critical tissue regions of the patient and using a shading of the second color range, the shading of the second color range representing the dose distribution information in the anatomical body parts belonging to the second eligibility class assigned to the critical tissue regions of the patient, wherein the second color range is disjoint to the first color range; and
         a third color range assigned to the anatomical body parts belonging to the third eligibility class assigned to the target tissue regions of the patient and using a shading of the third color range, the shading of the third color range representing the dose distribution information in the anatomical body parts belonging to the third eligibility class assigned to the target tissue regions of the patient, wherein the third color range is disjoint to the first and second color ranges.

19. A data processing system for displaying a radiation dose distribution of a treatment radiation in tissue of a patient, the system comprising:
   a non-transient memory;
   a computer operatively coupled with the non-transient memory; and
   a display device operatively coupled with the computer and with the non-transient memory;
   the computer comprising a processor configured to acquire medical image data comprising medical image information describing a plurality of anatomical body parts of the patient;
   the processor being further configured to acquire, based on the medical image data, irradiation eligibility data comprising irradiation eligibility information describing an eligibility class to which each anatomical body part of the plurality of anatomical body parts belongs, each eligibility class describing a measure of desirability of irradiating a corresponding anatomical body part with the treatment radiation;
   the processor being further configured to acquire dose distribution data comprising dose distribution information describing the radiation dose distribution in the plurality of anatomical body parts; and
   the display device being configured to display the dose distribution information colorized in the medical image information and graphically overlaid with an image of the plurality of anatomical body parts, the displaying of the dose distribution information colorized in the medical image information being based on the irradiation eligibility data and based on using a color shading that represents the dose distribution information in the plurality of anatomical body parts, wherein, for each selected eligibility class, a unique color range is assigned to one or more anatomical body parts belonging to the each selected eligibility class for the displaying.

20. The system according to claim 19, wherein:

the processor is further configured to acquire the irradiation eligibility data comprising irradiation eligibility information describing:

a first eligibility class assigned to healthy tissue regions of the patient to which a first set of one or more anatomical body parts of the plurality of anatomical body parts belong, the first eligibility class describing a moderate measure of desirability of irradiating a corresponding anatomical body part member of the first eligibility class with the treatment radiation, wherein irradiation is acceptable but not desired;

a second eligibility class assigned to critical tissue regions of the patient to which a second set of one or more anatomical body parts of the plurality of anatomical body parts belong, the second eligibility class describing a low measure of desirability of irradiating a corresponding anatomical body part member of the second eligibility class with the treatment radiation, wherein irradiation is unacceptable and not desired; and a third eligibility class assigned to target tissue regions of the patient to which a third set of one or more anatomical body parts of the plurality of anatomical body parts belong, the third eligibility class describing a high measure of desirability of irradiating a corresponding anatomical body part member of the third eligibility class with the treatment radiation, wherein irradiation is acceptable and desired; and the display device is configured to display the dose distribution information colorized in the medical image information and graphically overlaid with the image of the plurality of anatomical body parts based on:

a first color range assigned to the anatomical body parts belonging to the first eligibility class assigned to the healthy tissue regions of the patient and using a shading of the first color range, the shading of the first color range representing the dose distribution information in the anatomical body parts belonging to the first eligibility class assigned to the healthy tissue regions of the patient;

a second color range assigned to the anatomical body parts belonging to the second eligibility class assigned to the critical tissue regions of the patient and using a shading of the second color range, the shading of the second color range representing the dose distribution information in the anatomical body parts belonging to the second eligibility class assigned to the critical tissue regions of the patient, wherein the second color range is disjoint to the first color range; and a third color range assigned to the anatomical body parts belonging to the third eligibility class assigned to the target tissue regions of the patient and using a shading of the third color range, the shading of the third color range representing the dose distribution information in the anatomical body parts belonging to the third eligibility class assigned to the target tissue regions of the patient, wherein the third color range is disjoint to the first and second color ranges.

* * * * *